United States Patent [19]
Bruno et al.

[11] Patent Number: 5,636,017
[45] Date of Patent: Jun. 3, 1997

[54] OPTICAL DETECTION ARRANGEMENT FOR SMALL VOLUME CHEMICAL ANALYSIS OF FLUID SAMPLES

[75] Inventors: Alfredo E. Bruno, Oberwil; Beat Krattiger, Riehen, both of Switzerland; Carlo S. Effenhauser, Weil am Rhein, Germany; Francois Maystre, Reinach, Switzerland; Philippe Nussbaum, Hegenheim, France

[73] Assignee: Ciba-Geigy Corporation, Tarrytown, N.Y.

[21] Appl. No.: 212,521

[22] Filed: Mar. 11, 1994

[30] Foreign Application Priority Data

Mar. 18, 1993 [EP] European Pat. Off. ............. 93810196

[51] Int. Cl.⁶ .................................................. G01N 21/05
[52] U.S. Cl. ....................................... 356/246; 356/440
[58] Field of Search .................................. 356/246, 361, 356/440, 417, 410; 250/574

[56] References Cited

U.S. PATENT DOCUMENTS

| | | | |
|---|---|---|---|
| 4,343,991 | 8/1982 | Fujiwara et al. | 250/227 |
| 4,816,123 | 3/1989 | Ogan et al. | 356/246 |
| 5,037,199 | 8/1991 | Hlousek | 356/410 |
| 5,120,387 | 6/1992 | De Bie | 156/250 |
| 5,192,412 | 3/1993 | Kambara et al. | 204/299 |
| 5,199,966 | 4/1993 | Harvey et al. | 65/4.21 |
| 5,324,401 | 6/1994 | Yeung et al. | 356/344 |

FOREIGN PATENT DOCUMENTS

| | | | |
|---|---|---|---|
| 0440577 | 8/1991 | European Pat. Off. | 356/361 |
| 454286 | 10/1991 | European Pat. Off. | |
| 476248 | 3/1992 | European Pat. Off. | |
| 4139211 | 11/1990 | Germany | |

OTHER PUBLICATIONS

C. Reijinga et al. Journal of Chromatography vol. 283, (1984) pp. 99–111 (no month).

A. Brunee et al. Analytical Chem. vol. 63 No. 23 Dec. 1, 1991, pp. 2689–2697.

N. Dovichi, Review of Scientific Instruments vol. 61, No. 12 (Dec. 1990) pp. 3653–3667.

Analytical Chem., Brunee et al., vol. 61 No. 80, Apr. 15, 1989 pp. 876–883.

*Primary Examiner*—Richard A. Rosenberger
*Attorney, Agent, or Firm*—George R. Dohmann

[57] ABSTRACT

An optical detection arrangement for small volume chemical analysis comprises a light source (22), a capillary tube (23) and a photoelectric detector (24). The arrangement of the light source (22) relative to the capillary tube (23) is such, that probing light (P) emitted from the light source (22) strikes a sample (S) to be analyzed, which is flowing through the capillary tube (23), whereas the photoelectric detector (24) is arranged relative to the capillary tube (23) such, that it is capable of detecting light comming from the capillary tube. The photoelectric detector (24) is connected with an evaluation electronics. Between the light source (22) and the capillary tube (23) the probing light (P) is guided essentially in a guiding means (26) which is made of a material having a refractive index gradient about perpendicular to the direction of propagation of the probing light (P), and which is connected to the capillary tube (23) such that probing light (P) exiting the guiding material (26) strikes the capillary tube (23). Preferably light emitting diodes (LEDs) or laser diodes are used as light source (22).

15 Claims, 6 Drawing Sheets

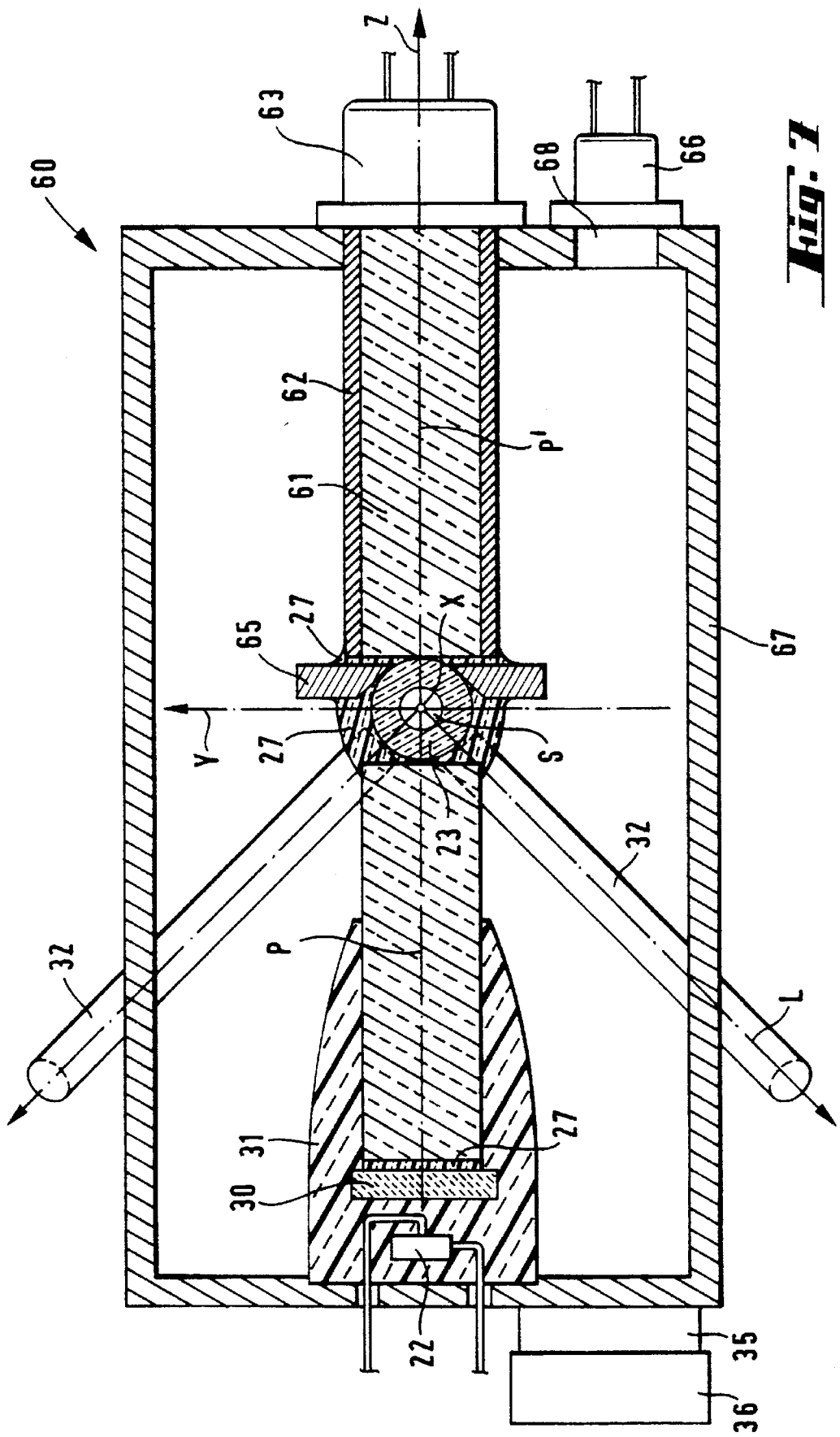

OPTICAL DETECTION ARRANGEMENT FOR SMALL VOLUME CHEMICAL ANALYSIS OF FLUID SAMPLES

The invention relates to an optical detection arrangement for small volume chemical analysis of fluid samples, as used for example in Capillary Electrophoresis (CE), in Micro-Column Chromatography, or in Capillary Chromatography, more particularly in High Performance Liquid Chromatography (HPLC).

BACKGROUND OF THE INVENTION

Capillary Electrophoresis (CE), Micro-Column Chromatography and Capillary Chromatography, more particularly High Performance Liquid Chromatography (HPLC), are well known techniques for liquid-phase chemical separation in small volume chemical analysis. There exists a great demand for improvements of the instrumental set-ups for these separation techniques, in order to achieve better separation results or a so-called higher number of theoretical plates, faster analysis times and lower reagent consumptions. Among the various aspects contributing to the overall performance in Capillary Electrophoresis (CE) and Micro-column and Capillary Chromatography (HPLC), the detection, which is most commonly performed by optical methods, is a very important one. There exists a great demand to be able to detect the substances of interest within nano-liter or even pico-liters volumes. Detection represents thus the main obstacle in the quest for higher miniaturization for small volume chemical analysis.

In Capillary Electrophoresis for example, to preserve the spatial profile of the eluting substances and, considering that the total volume of the separation stage, including the detection arrangement, is usually less than a milliliter, dead-volumes must be avoided. Under these circumstances it was found that meaningful results can only be achieved by on-column detection. This is also the case in HPLC. From the prior art several arrangements for on-column optical detection are known. These include detection arrangements for absorption, fluorescence, and refractive index measurements, as are described for example in N. J. Dovichi, Rev. Sci. Instrum. 61, 3653 (1990). There is, however, a growing demand to improve the sensitivity of those detection systems, to reduce their detection volumes while at the same time retaining the instrumental sensitivity.

Laser Induced Fluorescence (LIF) detection is, to date, considered to be one of the most sensitive detection methods for chemical separations in capillary tubes. However, even fluorescence detection methods based on conventional arc or filament lamps as excitation sources are suitable, although they are less sensitive.

The main advantages of lasers, as compared to conventional excitation sources, reside in their high intensifies and good spatial properties. However, both, lasers and conventional lamps display high fluctuations of their light intensities, which is very undesireable for detection purposes. Intensity fluctuations of the excitation source have a negative impact on fluorescence detection arrangements because they manifest in both, the fluorescence signal (S) and in the background noise (N). This latter because of the unavoidable amount of scattering light, which reaches the usually employed photomultiplier.

Fluorescence detectors operating without scattered light are known as background-free detectors. The baseline noise of these detectors is dominated by shot-noise. Background-free detectors are not uncommon for gas phase detection but they are more difficult to realize in the liquid phase, and it is even more difficult in the presence of liquid filled narrow bore capillary tubes. The difficulties arise primarily from the fact, that scattering light is produced at the four unavoidable optical interfaces in the light propagation media at the measuring zone. These difficulties are described in more detail for example in A. E. Bruno, B. Krattiger, F. Maystre and H. M. Widmer, Anal. Chem., 63, 2689 (1991). The four optical interfaces arise at the walls of the capillary tube and are the interfaces air/FS, FS/buffer, buffer/FS and FS/air, wherein FS refers to the capillary tube material, which normally is fused silica or another type of glass.

It is to be noted that scattering light is not only a major problem for fluorescence detectors, but also limits the resolution of other detector arrangements, such as for example for absorption, and refractive index measurements. In these detector arrangements, as well as in the ones for fluorescence measurements the baseline noise constitutes a major limiting factor for the application of the respective methods. The ultimate sensitivity of optical detectors employed is often limited by noise and drifts caused by the thermal expansions of the materials involved, by vibrations and Schlieren effects in the light propagation media, which starts at the light source and ends at the surface of the photoelectric detector. These noise and drift sources are mainly generated at the various optical interfaces, where reflection and refraction takes place, and, they are more pronounced when the interfaces encountered are not flat but have a curvature, like in the case of lenses or round capillaries.

In the past solutions have been proposed to minimize the amount of scattering light reaching the photosensitive devices such as the photosensitive detector and the photomultipliers. One of these approaches is described for example in N. J. Dovichi, Rev. Sci. Instrum. 61, 3653, (1990). The approach consists in the elimination of all optical interfaces in the area of the measuring zone. The socalled "windowless cell" is known as "sheath flow cuvette" and is arranged at the end of the capillary tube. Unfortunately this approach is not particularly easy to implement and only few optical detectors can be constructed in the proposed manner.

In indirect fluorescence detection arrangements the baseline noise is almost entirely due to the noise of the fight source. In indirect fluorescence the solvent or buffer used in the separation is doped with a low concentration of a fluorophore. Elution of non-fluorescent ionic analytes, instead of diluting the solvent, displaces the fluorescent dye. The detection of the substances of interest is accomplished by monitoring the decrease in the fluorescence (i.e. a fluorescence dip) due to a decrease in the concentration of the buffer or solvent. From the outlined detection principle it is easily conceivable that intensity fluctuations of the excitation light source are detrimental to the measurements.

SUMMARY OF THE INVENTION

It is therefore an object of the present invention to overcome the aforementioned disadvantages of the detection arrangements in particular for samll volume chemical analysis known from the prior art. There shall be provided a detection arrangement, which reduces the baseline noise. The detection arrangement shall be mechanically stable to minimize the effect of, for example, vibrations, and thermal expansions because of temperature differences and due to different coefficients of thermal expansion of the different materials involved in the construction. Optical instabilities due to intensity fluctuations of the light source and due to scattering light at interfaces shall be reduced and avoided. The detection arrangement shall be applicable for various different types of detection methods, such as for absorption, fluorescence, and refractive index measurements. In particular for detection methods employing direct or indirect fluorescence methods a detector arrangement shah be provided, which overcomes the problem of intensity fluctuations of the exciting light source. There shall also be provided a detection arrangement, that is easily miniaturizable, in order to meet the strongly desired objects of faster analysis times and lower reagent consumptions. Dead volumes shall be avoided in order to be able to detect the substances of interest in quantities of nano-liters or even of pico-liters.

These and further objects of the present invention are achieved by an optical detection arrangement for small volume chemical analysis of fluid samples, as used for example in Capillary Electrophoresis (CE) or in Micro-Column Chromatography and in Capillary Chromatography, more particularly in High Performance Liquid Chromatography (HPLC), which comprises a light source, a capillary tube and a photoelectric detector. The arrangement of the light source relative to the capillary tube is such, that probing light emitted from the light source strikes a sample to be analyzed, which is flowing through the capillary tube, whereas the photoelectric detector is arranged relative to the capillary tube such, that it is capable of detecting light comming from the capillary tube. The photoelectric detector is connected to an evaluation electronics. Between the light source and the capillary tube the probing light is guided essentially in a guiding means which is made of a material having a refractive index which is comparable with the refractive index of the capillary tube and which has a refractive index gradient about perpendicular to the direction of propagation of the probing light. The guiding means is connected to the capillary tube such, that probing light exiting the guiding material strikes the capillary tube. By guiding the probing light between the light source and the capillary tube along a defined light path in a material, which is connected to the capillary tube, reflections at the capillary wall are minimized and thus the amount of scattering light is reduced.

The problem of intensity variations is solved by using light emitting diodes (LEDs) as light source. LEDs, when operated with stabilized power supplies, are orders of magnitude more stable than lasers and conventional light sources and have practically no intensity fluctuations.

BRIEF DESCRIPTION OF THE DRAWINGS

Further objects and advantageous features of the claimed invention will become apparent from the description of exemplary embodiments of the invention with reference to the accompanying drawings. In the schematic drawings:

FIG. 7 is a fifth embodiment of a detection arrangement according to the invention sectioned along a plane normal to the axis of a capillary tube.

DETAILED DESCRIPTION OF PREFERRED EMBODIMENTS

Figure 1:
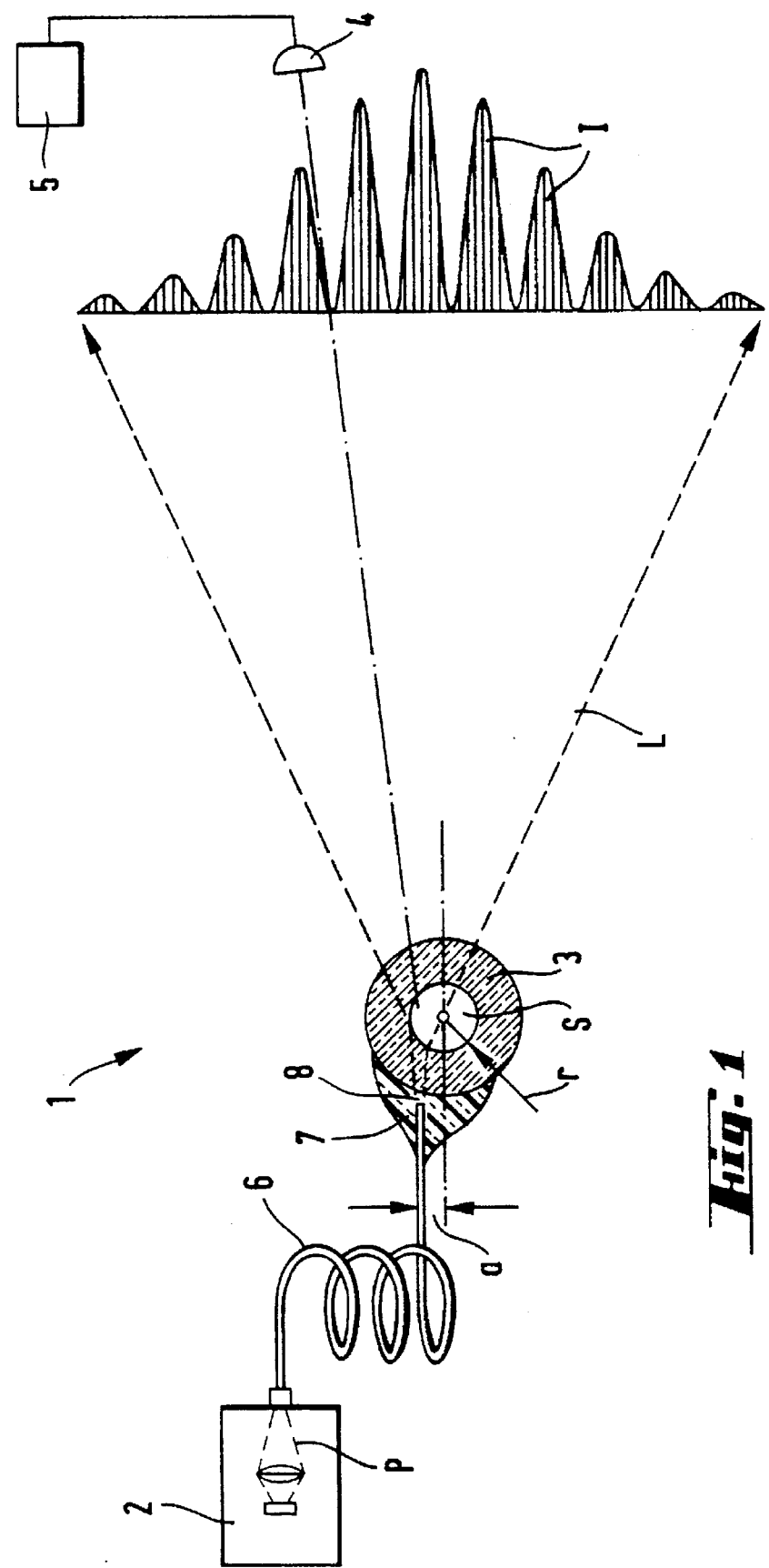
FIG. 1 is a representation of a first embodiment of a detection arrangement according to the invention.

In FIG. 1 a schematic representation of a first embodiment of an optical detection arrangement according to the invention is generally designated with the reference numeral 1. More specifically, this first embodiment of a detection arrangement is an interferometric apparatus particularly for monitoring changes of the refractive index of fluid samples flowing through a capillary tube. The principles of such an interferometric detection arrangement are described for example in Analytical Chemistry, Vol. 63, No. 23, (1991), pages 2689–2697; therefore the subsequent description of this first embodiment of the invention is reduced to the essentials necessary to understand the invention.

The interferometric detection arrangement 1 comprises a light source 2, a capillary tube 3 and a photoelectric detector 4. The arrangement of the light source 2 relative to the capillary tube 3 is such, that probing light P emitted from the light source 2 strikes a sample S to be analyzed, which is flowing through the capillary tube 3, whereas the photoelectric detector 4 is arranged relative to the capillary tube 3 such, that it is capable of detecting light L comming from the capillary tube 3. The superposition of the light L reflected from the inner optical interface of the capillary tube 3 and from the sample, respectively, results in an interference pattern I, which is monitored by the photoelectric detector 4. In this first embodiment the photoelectric detector 4 is preferably a position sensitive diode and is connected with an evaluation electronics 5. Upon changes of the refractive index of the sample flowing through the capillary tube 3 the interference fringe pattern I changes its shape and is shifted. The changes of the fringe pattern I are detected by the photoelectric detector 4. The resulting electric signals are passed on to the evaluation electronics 5 for amplification, transformation and evaluation. So far the interferometric detection arrangement corresponds to the ones known from the prior art.

According to the invention the probing light P is guided between the light source 2 and the capillary tube 3 essentially in a guiding means 6, which is made of a material having a refractive index comparable to that of the capillary tube 3, and which has a refractive index gradient about perpendicular to the direction of propagation of the probing light. The probing light guiding means 6 is connected to the capillary tube 3 such, that probing light P exitting the guiding material strikes the sample S flowing through the capillary tube 3.

In the first embodiment of the invention the probing light guiding means 6 is an optical waveguide, preferably a single-mode optical fiber, which preserves the state of polarization of the probing light P. One end of the optical fiber 6 is connected to the capillary tube 3. The transition region 8, where the optical fiber 6 and the capillary tube 3 are connected, has a refractive index, which matches the refractive index of the wall of the capillary tube 3 within a boundary of about +20%. The connection between the optical fiber 6 and the wall of the capillary tube 3 can be achieved by directly soldering the interfaces. In a preferrend variant of the invention the connection between the optical fiber 6 and the capillary tube 3 is achieved by gluing them together with a transparent adhesive, which has a refractive index, that matches the refractive index of the wall of the capillary tube 3 within about ±20%. Suitable adhesives are for example two component ashesives, such as the ones marketed by the applicant.

Figure 2:
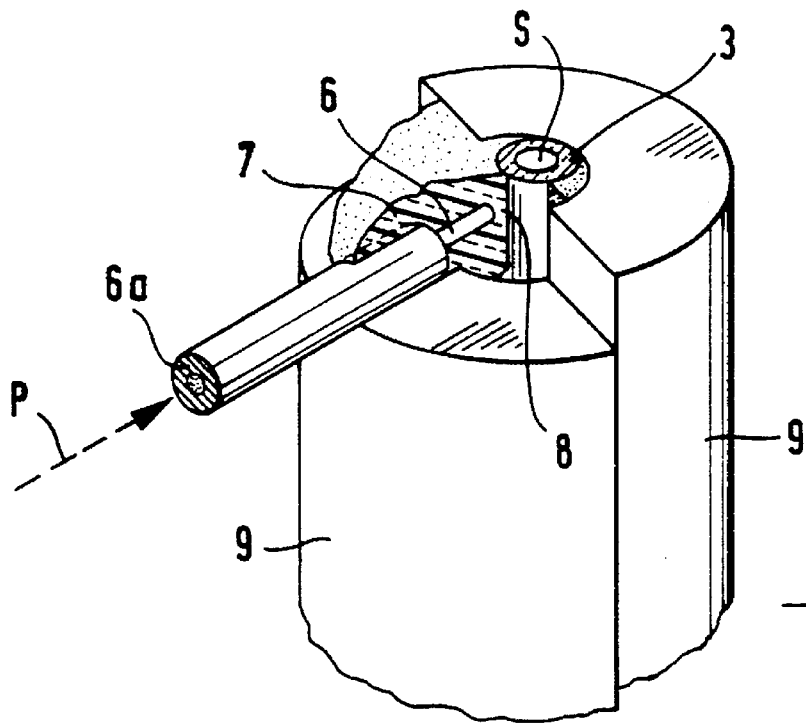
FIG. 2 is a partly sectional view of a transition region between a capillary tube (sectioned) and an optical fiber in the embodiment of the invention according to FIG. 1.

In FIG. 2 the connection of the optical fiber 6 with the capillary tube 3 is shown in more detail. The capillary tube 3 is embedded in two halves of a glass tube 9. At the front end of the optical fiber 6 the coating 6a is removed. The optical fiber 6 is placed onto the top face of one of the halves and its front end moved into close vicinity of the wall of the capillary tube 3. An amount of a suitable transparent adhesive 7 is poured over the arrangement and cured. In this case so-called UV-adhesive that are curable by exposure to ultraviolett radiation (UV-light)are preferred in order to make the final adjustments more easily. The UV-adhesive will only be cured, when the adjustment of the optical fiber is satisfactory, by a simple irradiation with UV-light.

Figure 3:
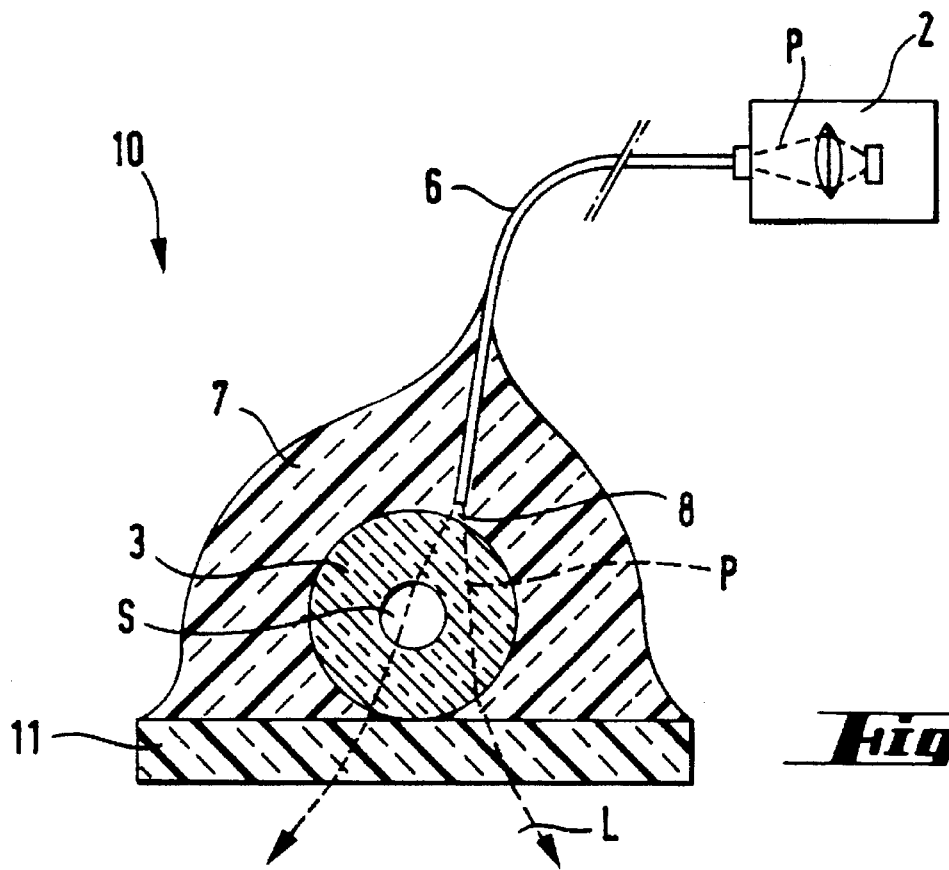
FIG. 3 is a second embodiment a detection arrangement according to the invention.

In FIG. 3 a second embodiment of an interferometric detection arrangement is depicted. In FIG. 3 emphasis has been placed only on the "probing light part" of the arrangement. The detection and evaluation part has not been shown, because it is conventional and comparable to the one in FIG. 1. In this second embodiment, which is generally designated with reference numeral 10, the capillary tube 3 is fixed onto a microscope slide 11. It is to be understood that any other transparent support is suitable, provided its refractive index is close to the refractive index of the capillary tube. A suitable transparent adhesive, which is preferably UV curable, is poured over part of the capillary tube 3. After the optical fiber has been adjusted the adhesive is cured. The optical fiber 6 is adjusted under a special angle with respect to a perpendicular line on the surface of the microscope slide 11. More particularly, the angular adjustment of the optical fiber 6 is such, that the fringe pattern I of interest leaves the microscope slide 11 in a direction parallel to the perpendicular line. The fringe pattern is generated by recombination of a (sample) penetrating part and a (sample surface) reflected part of the incoming probing light beam.

From FIGS. 1 and 3 it can easily be derived that the optical waveguide 6 is arranged to be off-axis with respect to the axis of the capillary tube 3 by a distance a. By this arrangement a fringe pattern is obtained, which displays a high contrast. In a preferred embodiment of the invention the optical waveguide 6 is mounted to the capillary tube such, that the probing beam P strikes the sample S flowing through the capillary tube 3 about tangentially. The off-axis distance a, at which the optical waveguide 6 is mounted with respect to the capillary tube axis amounts preferably to about the internal radius r of the capillary tube. The probing beam P has its beam waist at the exit end of the optical waveguide 6. As the beam expands after exitting the optical waveguide 6, its beam width increases. When the beam hits the sample within the capillary tube the beam diameter should preferably be within 1/5–1/1 of the internal radius r of the capillary tube 3

The optical waveguide 6 is preferably connected to the light source 2. The connection is established best by conventional means with a transparent adhesive. If desired one or more lenses, preferably gradient index lenses, so-called GRIN lenses can be connected to the assembly between the light source 2 and the optical waveguide 3. Thus, the light source 2, preferably a laser diode, which emits either coherent or non-coherent light, the optical waveguide 6, preferably a polarization preserving single-mode optical fiber, and the capillary tube 3, which is preferably made of fused silica, form an interconnected assembly, free of optical interfaces, which is mechanically rigid and which has thermally coupled joints. Therefore, mechanical vibrations do not disturb the probing light path, and thermal influences are distributed along the joints fast such, that temperature differences can be neglected. This, and because the materials of the optical waveguide 6 and of the capillary tube 3 have comparable coefficients of thermal expansion, thermal influences on the baseline noise are practically avoided.

Figure 4:
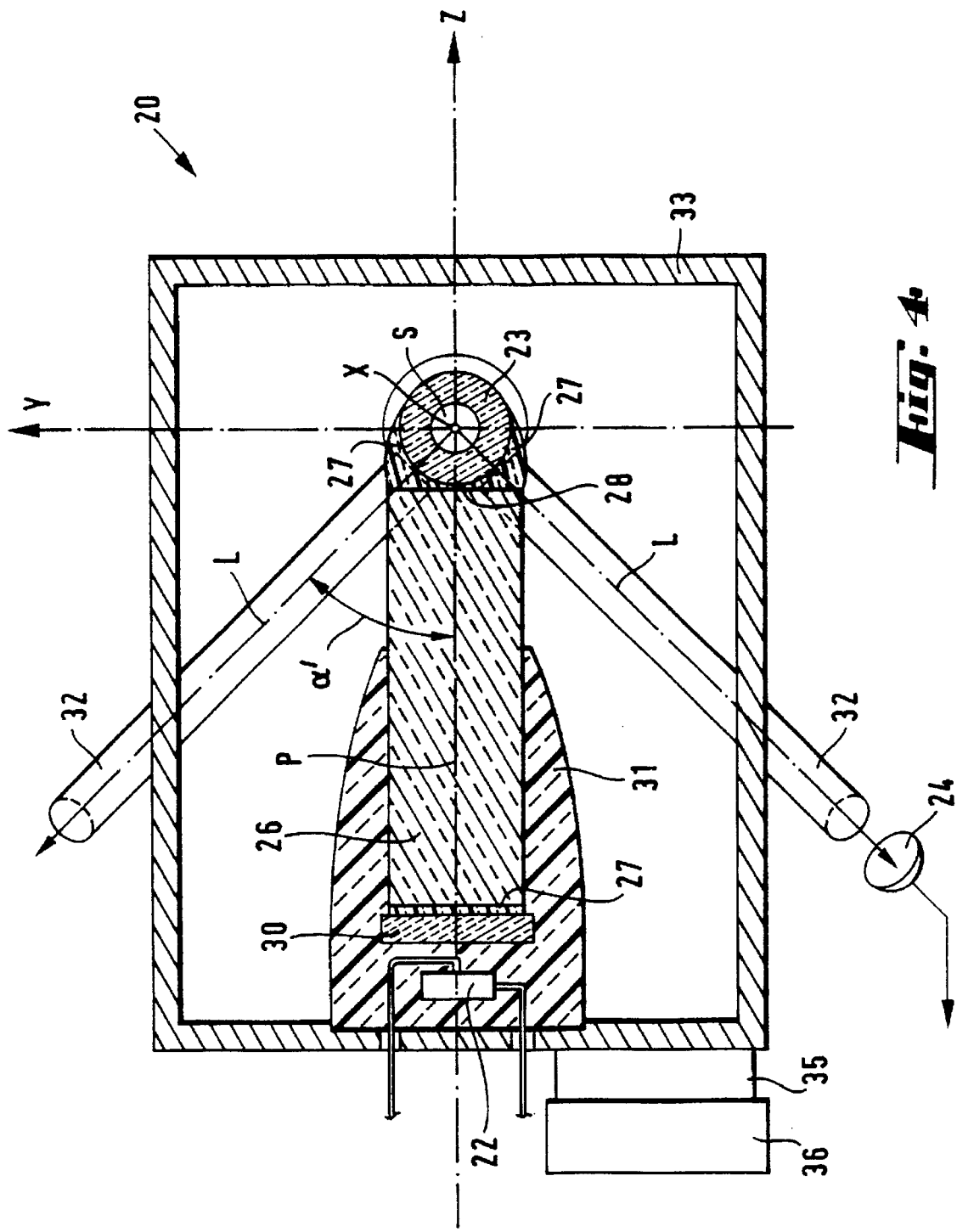
FIG. 4 is a third embodiment of a detection arrangement according to the invention sectioned along a plane normal to the axis of a capillary tube.
Figure 5:
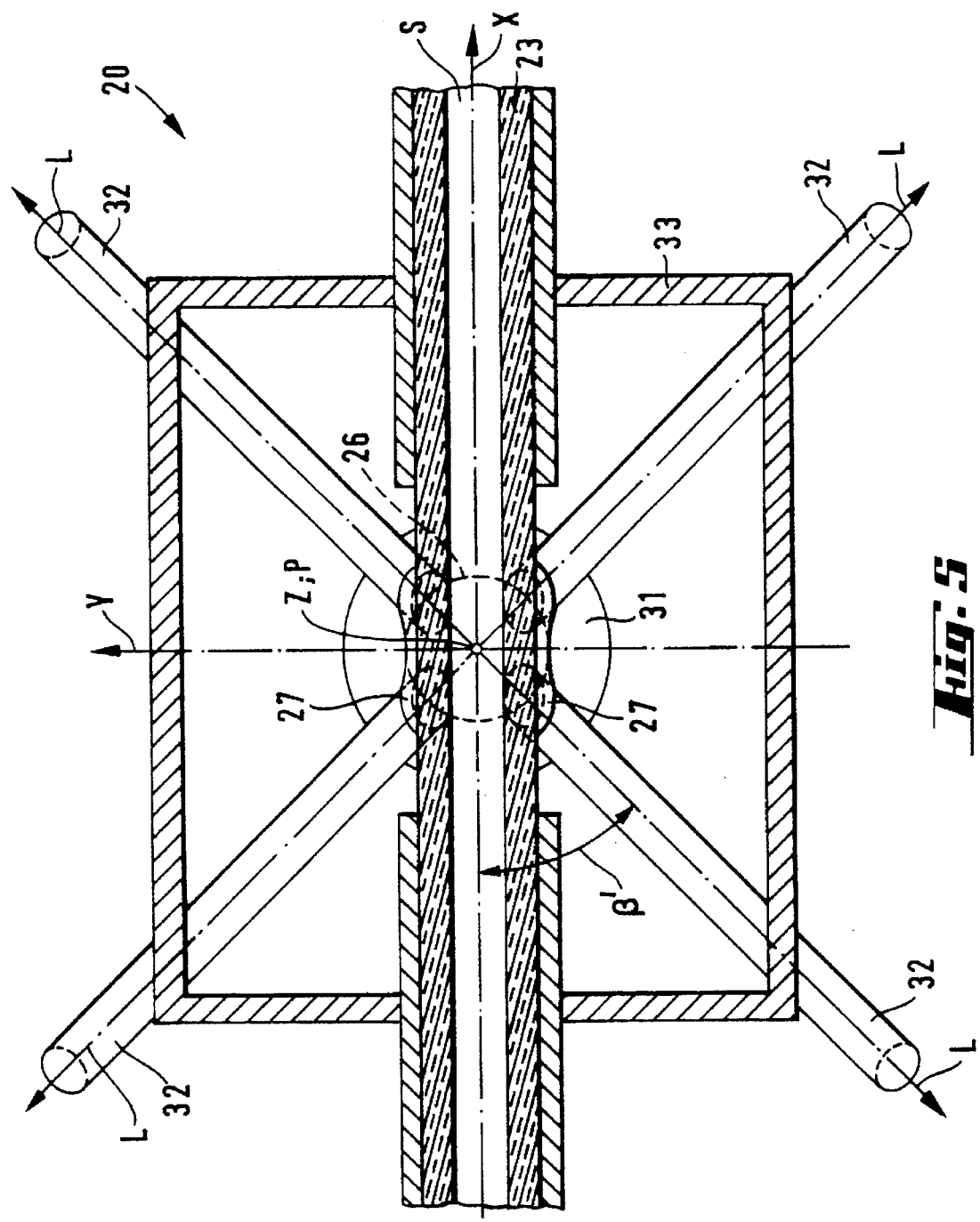
FIG. 5 is a view of the embodiment according to FIG. 4 sectioned along the axis of the capillary tube.
Figure 6:
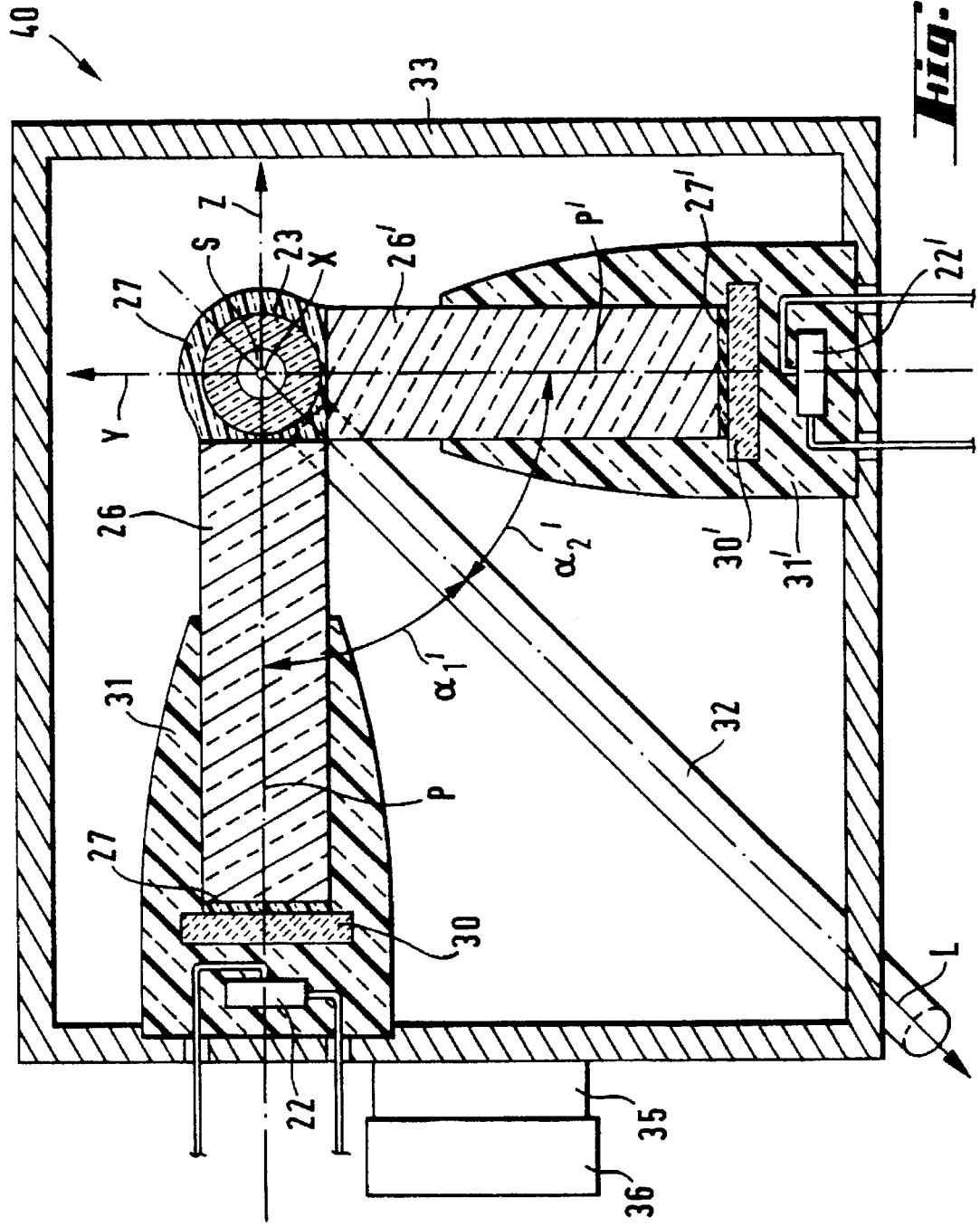
FIG. 6 is a fourth embodiment of a detection arrangement according to the invention sectioned along a plane normal to the axis of a capillary tube.

While the embodiments of the invention according to FIGS. 1–3 depict an interferometric detection arrangement, FIGS. 4–6 show examplary embodiments of detection arrangements according to the invention, which are based on the principle of fluorescence. In FIG. 7 there is depicted a further embodiment of the detection arrangement, which is based on both, the principle of fluorescence and that of absorption. The fluorescence detection arrangement in FIGS. 4 and 5 is shown in two sectioned views, wherein in FIG. 4 the detection arrangement is sectioned along a plane perpendicular to the extension of the capillary tube, and FIG. 5 shows the same detection arrangement sectioned along the axis of the capillary tube. In FIGS. 4 and 5 the exemplary embodiment of the detection arrangement is generally designated with the reference numeral 20. It comprises, in analogy to the interferometric detection devices 1 and 10 described before, a light source 22, a capillary tube 23 and a photoelectric detector 24. The arrangement of the light source 22 relative to the capillary tube 23 is such, that probing light P emitted from the light source 22 strikes a sample S to be analyzed, which is flowing through the capillary tube 23, whereas the photoelectric detector 24 is arranged relative to the capillary tube 23 such, that it is capable of detecting fluorescent light L emitted from the sample S flowing through from the capillary tube 23.

According to the invention between the light source 22 and the capillary tube 23 there is arranged a probing light guiding means 26, which is made of a material, which has a refractive index gradient about perpendicular to the direction of propagation of the probing light. The probing light guiding means 26 is connected to the capillary tube 23 such, that probing light P exitting the guiding material strikes the capillary tube 23. As in the interference type detection arrangements 1, 10 the transition region 28, where the probing light guiding means 26 is connected with the capillary tube 23, has a refractive index, which matches the wall material of the capillary tube within about +20%. The connection between the probing light guiding means 26 and the wall of the capillary tube 23 can be achieved by gluing processes or by directly soldering the interfaces as indicated above. In a preferrend variant of the invention the connection between the guiding means 26 and the capillary tube 23 is achieved by gluing them together with a transparent adhesive, which has a refractive index, that matches the refractive index of the wall of the capillary tube 23 within about ±20%. Suitable adhesives are the same ones as described before in connection with the interference type detection arrangements. The location of the probing light guiding means 26 relative to the capillary tube 23 is such, that the waist of the probing beam P is located within the sample S flowing through the capillary tube 23.

In one embodiment of the invention the probing beam guiding means 26 is a gradient refractive index optical element, or a GRIN-lens, preferably selected from the ones with the brand name SelFoc®, as available, from NIPPON SHEET GLASS Co. Ltd. In another embodiment of the invention the probing light guiding means 26 is an optical waveguide, preferably a multi-mode optical fiber.

The end of the probing light guiding means 26, where the probing light exits, is connected to the capillary tube 23. Between the light source 22 and the probing light guiding means 26 there are preferably arranged optical interference and/or cut-off-filters 30 for selecting the wavelength(s) of the probing light P. These filters 30 are also connected with the probing light guiding means 26, preferably they are glued together with an adhesive 27 corresponding to the adhesive used for establishing the connection to the capillary tube 23. The light source 22 can also be glued to the filters 30, however, preferably the light source 22, the filters 30 and the rear end of the probing light guiding means 26 are embedded preferably in a plexiglas housing 31.

In a most preferred embodiment of the invention, which employs both, the principle of absorption and that of fluorescence, the light source 22 is a light emitting diode (LED), which, when operated with stabilized power supplies, is a very stable light source. If there is the need for a greater intensity at the capillary tube 23, two or more LEDs can be assembled to an LED-array. Such LED-arrays can comprise LEDs emitting at the same wavelength, or different LEDs emitting light at different wavelengths. The desired wavelength(s) can then be selected by interference or cut-off filters 30 in the probing light path.

In order to assemble the light source 22, the filter(s) 30 and the rear end of the probing light guiding means 26 in the plexiglas housing 31, which usually forms an integral part of the LED, first a hole is drilled into the housing 31. The deepness of the hole in the original housing of the LED reaches the immediate vicinity of the LED crystal 22, in order to be able to place the GRIN-lens or the optical fiber, respectively, as close as possible to the LED crystal 22. When one or more interference or cut-off filters are needed to select a portion of the emission spectrum of the LED they are most conveniently placed into the drilled hole in the housing 31, between the LED crystal and the GRIN-lens or the waveguide, respectively. Preferably the elements in the hole are connected with a transparent refractive index matching adhesive of the aforementioned type. The other end of the GRIN-lens or the optical waveguide 26 is connected to the capillary tube 23 using suitable transparent refractive index matching adhesives or soldering methods. The connection is such, that the center of the capillary tube is at, or near, the focal point of the GRIN-lens for the most efficient illumination of the sample S flowing through the capillary tube 23.

Between the capillary tube 23 and the photoelectric detector 24 and connected to the capillary tube 23 there is at least one sample light guiding means 32, which is made of a material, that has a refractive index gradient about perpendicular to the direction of propagation of the sample light comming from the capillary tube 23, and which is capable of guiding the collected sample light L to the photoelectric detector 24. The transition region, where the sample light guiding means 32 is connected with the capillary tube 23, has a refractive index, which approximately matches that of the wall material of the capillary tube 23 within about +20%. As can be seen in more detail in FIG. 5, the fluorescence detection arrangement 20 comprises four sample light guiding means 32, which are adapted to guide a certain portion of the light L, which is emitted from the excited sample, or in the case of indirect fluorescence from an additive within the sample, to one or more photoelectric detectors 24. In FIG. 4 there is one photoelectric detector drawn schematically. It is understood, that the detector(s) 24 are connected with an evaluation unit, where the detected signals are amplified, transformed and evaluated according to given criteria. The evaluation unit is conventional, therefore it is not shown in the drawings.

In one embodiment of the invention the sample light guiding means 32 are optical fibers, which are connected to the capillary tube at one end, and which guide the sample light L onto photoelectric detectors, which are located at their other ends. Preferably the photoelectric detectors are also connected to the optical fibers with a transparent and refractive index matching adhesive. In another embodiment the sample light guiding means 32 are so-called GRIN-lenses, which direct the sample light L to four separate photoelectric detectors or to one common photoelectric detector. If desired, there may be arranged somewhere between the sample light guiding means and the photoelectric detector(s) optical interference and/or cut-off-filters, which allow to select specific wavelengths of the emitted fluorescence light from the sample volume within the capillary tube 23.

In the embodiment of the fluorescence detection arrangement 20 shown in FIGS. 4 and 5 most of the scattered light, which originates from reflections at the inner optical interfaces of the capillary tube 23 shows its maximum intensity in the plane defined by the axes Y and Z in FIG. 4. For this reason it is convenient, not to place the collecting optical elements (optical waveguides or GRIN-lenses, filters, detectors) in this YZ plane. Therefore, in the preferred embodiment of the fluorescence detection arrangement 20 shown in FIGS. 4 and 5 the optical waveguides or the GRIN-lenses, respectively, are arranged along the circumference of the capillary tube such, that their axes are inclined with respect to the axis X of the capillary tube (angle 13' in FIG. 5) and also with respect to the direction of propagation Z of the probing light (angle $\alpha'$ in FIG. 4). It is to be noted that in FIGS. 4 and 5 only the projections of the collecting optical elements into the YZ plane and the XY plane, respectively, and thus the projections $\alpha'$ and $\beta'$ of the real angles in space are shown. The real angles in space, both, amount to about 20°–70°, preferably to about 54.7°±10° with respect to the axis of the capillary tube (3) and to the inverted direction of propagation of the probing light P.

As shown in FIG. 4 and 5, the elements of the detection arrangement 20 are housed within a light proof housing 33 having multiple orifices at various angles to assemble all components involved. The housing 33 has good heat conducting properties. Its temperature is preferably controlled by a Peltier element 35 and a heat sink 36, which are attached to the outside wall of the housing 33.

FIG. 6 shows a further embodiment of a detection arrangement which is also based on fluorescence. This exemplary embodiment is generally designated with the reference numeral 40. The detection arrangement 40 comprises two excitation light sources 22, 22', which are arranged perpendicular with respect to each other in front of the capillary tube 23. The construction and the set-up of the probing light part of the arrangement in front of the capillary tube 23 basically corresponds to the embodiment depicted in FIGS. 4 and 5 the excitation light sources 22, 22' preferably are LEDs or LED-arrays, which emit either coherent or non-coherent light. As in the embodiment depicted in FIGS. 4 and 5 the collecting optical elements are inclined with respect to the axis of the capillary tube and also with respect to the directions of propagation Y and Z, respectively, of the two excitation light beams. In FIG. 6 only the projections $\alpha_1'$ and $\alpha_2'$ of the real angles in space are shown. The real angles in space amount to about 20°–70°, preferably to about 54.7°±10° with respect to the axis of the capillary tube 23 and to the inverted directions of propagation of the two probing light beams. The detection arrangement according to FIG. 6 allows to detect fluorescence light L, which is emitted from the sample S flowing through the capillary tube 23, as a result of equal or different excitation wavelengths of the probing light P. If the LEDs 22, 22' emit at the same wavelength, then the intensity of the probing light is increased, more light is radiated onto the sample volume, more fluorescence centers are thus excited, and therefore the sensitivity of the fluorescence detection arrangement is increased.

In FIG. 7 another embodiment of a detection arrangement is depicted. This embodiment is based on both, the principle of fluorescence and that of absorption. The LED based embodiment is designated with the reference numeral 60. It is designed for the simultaneous measurement of fluorescence and absorbance of a sample S flowing through the capillary tube 23. The side to the left of the capillary tube 23 basically corresponds to the embodiment depicted in FIGS. 4 and 5. On the right hand side of the capillary tube 23, there is shown a second GRIN-lens or an optical waveguide 61, respectively, which is located coaxial with the direction of propagation Z of the probing light P comming from the light source 22. This second GRIN-lens or optical waveguide, respectively, directs that portion P' of the probing light P that crosses the sample S, which flows through the capillary 23, to a photosensitive device 63, preferably a photodiode. To ensure that only light, which comes from the light source 22 and has transversed the capillary tube 23, reaches the photodiode 63, a slit 65 is placed into the light path, behind the capillary tube 23. Preferably the slit 65 is located between the capillary tube 23 and the second GRIN-lens or optical waveguide 61, respectively. The width of the slit 65 preferably about corresponds to the internal diameter of the capillary tube 23. A light-tight 62 tube around the second GRIN-lens or optical waveguide 61, respectively, prevents stray-light from reaching the photodiode 63. Beneath the photosensitive device 63 a second photoelectric diode 66 is arranged adjacent to a transmittant window portion 68 of a light-tight housing 67 for the detection arrangement 60. From a comparison of the amount of light P from the light source 22, with the portion of light P', which has transversed the capillary tube 23 and reaches the photodiode 63 with that detected by the second photoelectric detector 66, it is possible to correct for the noise caused by intensity fluctuations of the light source. For that type of measurement a special evaluation electronics, which is capable of computing data from relative measurements, is employed. Such, the instrumental sensitivity is further increased.

It is to be noted that the capillary tube can also have a rectangular or square cross-section. The capillary tube can also be made of one or more channels, which are etched or micro-machined into a planar glass structure. The light source can be a semiconducting light source, such as, for example a semiconductor laser or array. Detection arrangements according to the invention typically have capillary tubes 3, 23 with internal radii of from about 2.5 µm to about 125 µm. The capillary tubes 3, 23 usually are provided with a polyimide coating, which is removed only in the contact region with the guiding means for the probing light P.

By the detection arrangements according to the invention the three problems of optical, mechanical and thermal nature are addressed simultaneously. The detection arrangement has a very high mechanical and thermal stability because:

i) at least the probing light propagates, except for those at the two inner optical interfaces of the capillary tube, without refractions or reflections, provided the refractive indices of the components and, if applicable, of the adhesive match within ±20%, ii) the optical components are arranged into the most rugged construction possible and, iii) heat propagates rapidly.

In the case of so-called one-photon excitation emission occurs at longer wavelengths than excitation (i.e. $\lambda$, {excitation}<{emission}). Cut-off and interference filters are thus employed to reduce scattering light, which contributes to the socalled baseline noise of the chromatogram or electropherogram in question, which is caused basically by instabilities of the excitation light intensity. Considering now that the intensity stability of LEDs can be stabilized to better than $10^{-5}$, by using LEDs as light source the baseline noise can be kept very low even without optical filters and thus in the presence of scattered light.

In the so-called indirect fluorescence detection methods the baseline noise is almost entirely due to the noise of the light source. The solvent or buffer used in the separation is doped with a low concentration of a fluorophore. Elution of non-fluorescent analytes by diluting the solvent, displaces the fluorescent dye. The detection of the substances of interest is accomplished by monitoring the decrease in the fluorescence (i.e. a fluorescence dip) due to a decrease in the concentration of the buffer or solvent. Thus, the use of intensity-wise stable LEDs as light source for indirect fluorescence detection reduces the baseline noise.

What is claimed is:

1. An optical detection arrangement for small volume chemical analysis of fluid samples, comprising a light source, a capillary tube and a photoelectric detector, which is connected with an evaluation electronics, wherein the arrangement of the light source relative to the capillary tube is such, that probing light emitted from the light source strikes a sample to be analyzed, which is flowing through the capillary tube, whereas the photoelectric detector is arranged relative to the capillary tube such, that it is capable of detecting sample light coming from the capillary tube, wherein probing light is guided between said light source and said capillary tube essentially in a probing light guiding means, which is made of a material having a coefficient of thermal expansion comparable to the coefficient of thermal expansion of the capillary tube and a refractive index gradient about perpendicular to a direction of propagation of said probing light, and which is connected to said capillary tube in a mechanically stable manner by means of a light transparent adhesive having a refractive index which matches that of the wall material of said capillary tube within about 20%, the light guiding means being connected to the capillary tube such that said probing light exiting the guiding means travels through the transparent adhesive and strikes an inner wall of said capillary tube.

2. An optical detection arrangement according to claim 1, wherein between said capillary tube and said photoelectric detector there is at least one sample light guiding means connected to said capillary tube, which is made of a material, that has a refractive index gradient about perpendicular to the direction of propagation of said sample light comming from said capillary tube, and which is capable of guiding said collected sample light to said photoelectric detector.

3. An optical detection arrangement according to claim 2, wherein the sample light is guided from said capillary tube to said photoelectric detector by a sample light guiding means and a transition region between said sample light guiding means and said capillary tube has a refractive index which matches that of the wall material of said capillary tube within about ±20%.

4. An optical detection arrangement according to claim 3, wherein between said light source and said probing light guiding means there are arranged optical interference and/or cut-off filters for selecting specific wavelength of said probing light.

5. An optical detection arrangement according to claim 2, wherein between said sample light guiding means and said photoelectric detector there are arranged second optical interference and/or cut-off-filters.

6. An optical detection arrangement according to claim 5, wherein all optical elements, such as the light source, the probing light guiding means, the capillary tube, the sample guiding means, the photoelectric detector, and the optical interference and/or cut-off-filters are connected together by means of a transparent adhesive, which has a refractive index that matches that of the wall material of said capillary tube within about ±20%.

7. An optical detection arrangement according to claim 2, wherein said probing beam guiding means and said sample beam guiding means are optical waveguides.

8. An optical detection arrangement according to claim 7, wherein for said sample light there are provided more than one, preferably four optical waveguides as sample light guiding means, which are arranged along said capillary tube such, that their axes are inclined in space about 20°–70°, preferably 54.7°±20% with respect to a longitudinal axis of said capillary tube and to the inverted direction of propagation of said probing light, respectively.

9. An optical detection arrangement according to claim 2, wherein said probing beam guiding means and/or said sample beam guiding means are gradient refractive index optical elements, preferably GRIN-lenses.

10. An optical detection arrangement according to claim 1, wherein said light source is a light emitting diode emitting either coherent or non-coherent light.

11. An optical detection arrangement according to claim 1, wherein said light source comprises an array of light emitting diodes operating at the same or at different wavelengths.

12. An optical detection arrangement according to claim 1, wherein said probing beam guiding means is a polarization preserving single mode optical fiber.

13. An optical detection arrangement according to claim 12, wherein said optical fiber is mounted to said capillary tube such, that said probing beam strikes a sample flowing through said capillary tube about tangentially, with an off axis displacement with respect to a center of said capillary tube, that amounts to about the internal radius thereof, thus allowing one part of said probing light beam to traverse said sample while another part of said probing light beam is reflected at an inner wall of said capillary tube thus serving as a reference beam.

14. An optical detection arrangement according to claim 1, wherein said capillary tube has a rectangular or square cross-section.

15. An optical detection arrangement according to claim 1, wherein said capillary tube comprises one or more channels, that are etched or micro-machined into a planar substrate, such as, for example, glass, quartz and semiconducting materials.

* * * * *